United States Patent
Zhang et al.

(10) Patent No.: US 11,767,280 B2
(45) Date of Patent: Sep. 26, 2023

(54) PROCESS FOR MAKING PHENOL AND XYLENES

(71) Applicants: China Petroleum & Chemical Corporatoin, Beijing (CN); UOP LLC, Des Plaines, IL (US)

(72) Inventors: Shuguang Zhang, Wilmette, IL (US); Lubo Zhou, Deer Park, IL (US)

(73) Assignees: China Petroleum & Chemical Corporation, Beijing (CN); UOP LLC, Des Plaines, IL (US)

( * ) Notice: Subject to any disclaimer, the term of this patent is extended or adjusted under 35 U.S.C. 154(b) by 80 days.

(21) Appl. No.: 17/419,952

(22) PCT Filed: Feb. 4, 2019

(86) PCT No.: PCT/US2019/016536
§ 371 (c)(1),
(2) Date: Jun. 30, 2021

(87) PCT Pub. No.: WO2020/162877
PCT Pub. Date: Aug. 13, 2020

(65) Prior Publication Data
US 2022/0081382 A1    Mar. 17, 2022

(51) Int. Cl.
*C07C 37/50* (2006.01)
*C07C 6/12* (2006.01)
*C07C 37/72* (2006.01)

(52) U.S. Cl.
CPC ............. *C07C 37/50* (2013.01); *C07C 6/126* (2013.01); *C07C 37/72* (2013.01)

(58) Field of Classification Search
CPC ......... C07C 5/2729; C07C 34/72; C07C 5/00; C07C 6/126; C07C 15/08; C07C 37/50; C07C 39/04
See application file for complete search history.

(56) References Cited

U.S. PATENT DOCUMENTS 2,589,057 A    3/1952  Corson et al.
2,918,505 A    12/1959 Scott et al.
(Continued)

FOREIGN PATENT DOCUMENTS

DE    102014110489 A1    1/2016
GB       1232027           8/1967
(Continued)

OTHER PUBLICATIONS

International Search Report from PCT application No. PCT/IB2019/016536 dated Oct. 10, 2019.
(Continued)

*Primary Examiner* — Sharon Pregler

(57) ABSTRACT

Processes for making phenol and xylenes from a phenols-containing feed are described. The processes involve transalkylation of alkylphenols to form phenol and alkylbenzenes. The phenol is separated from the alkylbenzenes, and the alkylbenzenes may be separated into benzene, toluene, xylenes, and heavy alkylbenzene streams. The benzene stream may be recycled to the transalkylation reaction zone. The toluene may be sent to a disproportionation reaction zone, and the product is sent back to the aromatic separation zone. The toluene can also be recycled to the transalkylation zone. The xylenes are separated into a p-xylene stream and a mixed xylene stream comprising m-xylene and o-xylene. The mixed xylene stream is isomerized and the isomerized product is sent back to the aromatic separation zone. The heavy alkylbenzenes are dealkylated and separated, with the aromatic stream being recycled to the aromatic separation zone.

20 Claims, 1 Drawing Sheet

(56) References Cited

U.S. PATENT DOCUMENTS

| | | | |
|---|---|---|---|
| 3,110,745 A | 11/1963 | Peck et al. | |
| 3,151,175 A | 9/1964 | Goldsmith | |
| 3,188,359 A | 6/1965 | Lempert et al. | |
| 3,213,153 A | 10/1965 | Mills | |
| 3,236,904 A | 2/1966 | Pickert | |
| 3,281,483 A | 10/1966 | Benesi et al. | |
| 3,284,526 A | 11/1966 | Frayer et al. | |
| 3,417,149 A | 12/1968 | Neuworth et al. | |
| 3,418,380 A | 12/1968 | Laufer et al. | |
| 3,436,434 A * | 4/1969 | Lester | B01J 23/6522 502/313 |
| 3,597,492 A | 8/1971 | Otani et al. | |
| 3,790,642 A | 2/1974 | Kominami et al. | |
| 3,839,470 A | 10/1974 | Biller et al. | |
| 3,933,927 A | 1/1976 | Goddard | |
| 4,029,716 A | 6/1977 | Kaeding | |
| 4,149,019 A | 4/1979 | Alscher et al. | |
| 4,171,329 A | 10/1979 | Koniz et al. | |
| 4,554,388 A | 11/1985 | Keim et al. | |
| 5,866,740 A | 2/1999 | Mikitenko et al. | |
| 6,063,977 A | 5/2000 | Gajda et al. | |
| 6,797,849 B2 | 9/2004 | McMinn et al. | |
| 7,109,389 B2 | 9/2006 | Kong et al. | |
| 8,071,832 B2 | 12/2011 | Yoshikawa et al. | |
| 2013/0267744 A1 | 10/2013 | Kim et al. | |
| 2014/0100398 A1 | 4/2014 | Jin et al. | |

FOREIGN PATENT DOCUMENTS

| | | |
|---|---|---|
| GB | 1238353 | 7/1971 |
| GB | 1444935 | 8/1976 |
| JP | 2014500859 A | 1/2014 |
| JP | 2017521413 A | 8/2017 |
| RU | 2213124 C1 | 9/2003 |
| RU | 2664543 C3 | 11/2016 |
| WO | 2016012103 A1 | 1/2016 |
| WO | 2019103726 A1 | 5/2019 |
| WO | WO-2019103726 A1 * | 5/2019 ............ C07C 15/08 |
| WO | 2018225287 A1 | 6/2019 |

OTHER PUBLICATIONS

Written Opinion from PCT application No. PCT/IB2019/016536 dated Oct. 10, 2019.

Mavrodinova, Vesselina et al., Selective p-xylene formation upon toluene disproportionation over MCM-22 and ZSM-5 zeolites modified with indium, Catalysis Communications 6 (2005), 247-252.

Kaeding, W.W. et al., Shape-Selective Reactions with Zeolite Catalysts, Journal of Catalysis 69, 392-398 (1981).

Olah, George A., Nafion-H+ Catalyzed De-tert-butylation of Aromatic Compouds, J. Org. Chem., 1987, 52, 1881-1884.

Tashiro, M. et al., The Preparation of Alkylphenols using t-Butyl Function as a Positional Protective Group, Organic Preparations and Procedures International: The New Journal for Organic Synthesis, 8:6, 249-262, DOI: 10.1080/00304947609355638.

Yang, H. et al., Synthesis of Symmetry Substituted 2,6-Diphenylphenols, Depailment of Chemistry, McGill University, Canada, 1991.

Wu, Peng et al., Selective formation of p-xylene with disproportionation of toluene over MCM-22 catalysts, Microporous and Mesoporous Materials 22 (1998) 343-356.

Yoshikawa, Takuya et al., Conversion of Alkylphenol to phenol via transalkylation using zeolite catalysts, Catalysis Today (2018).

International Preliminary Report from corresponding PCT application No. PCT/US2019/016536 dated Aug. 19, 2021.

Search report from corresponding Russian application No. 2021120489, dated Jul. 12, 2022.

* cited by examiner

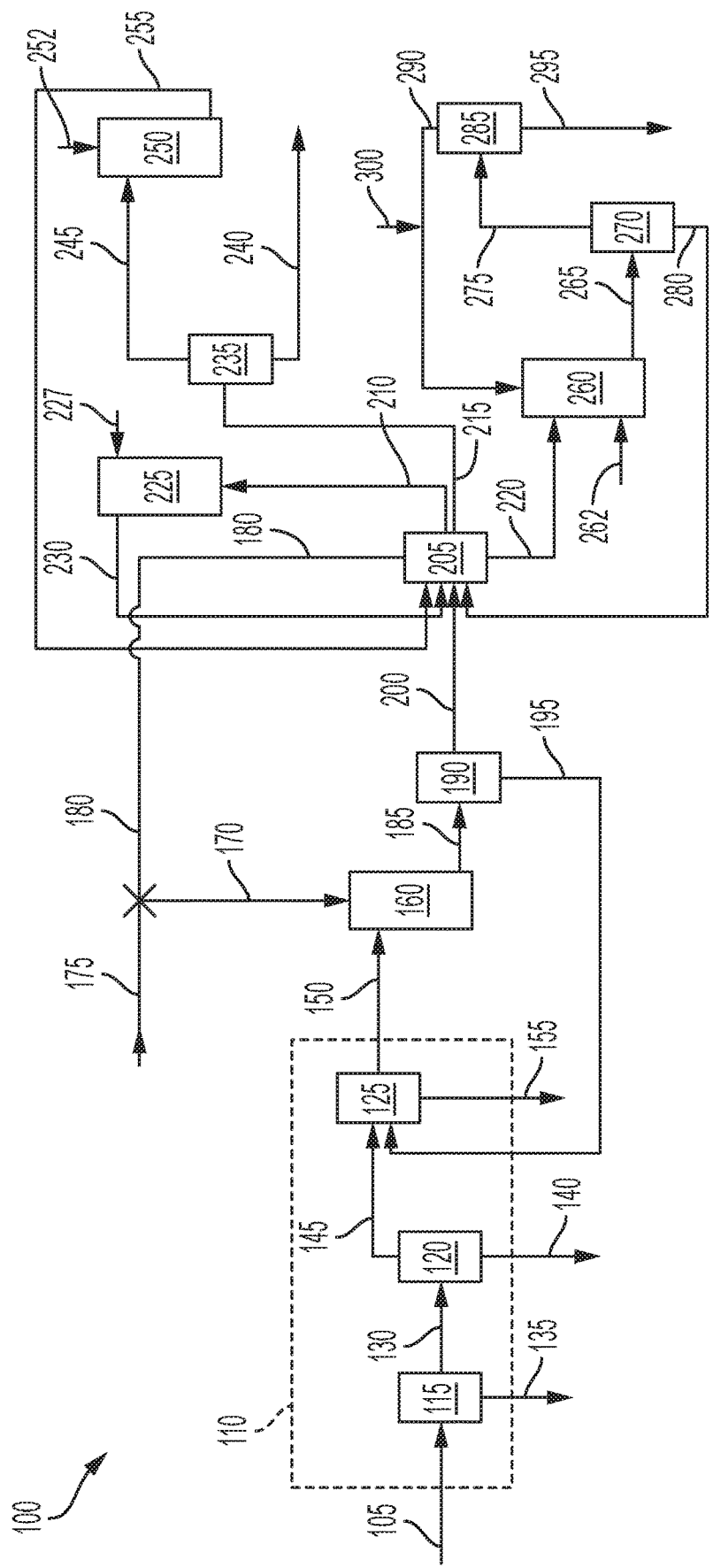

PROCESS FOR MAKING PHENOL AND XYLENES

This application is a U.S. National Phase under 35 U.S.C. § 371 of International Application No. PCT/US2019/016536 filed Feb. 4, 2019, which is incorporated herein by reference in its entirety.

BACKGROUND OF THE INVENTION

Many possible feeds include significant amounts of phenols which can be difficult to recover in a cost effective manner. For example, low and mid temperature coal tars are usually rich in phenolic compounds. Sometimes the content can be close to about 40 wt % of the coal tar stream. These phenols may be extracted from coal tar using various methods, such as washing with aqueous sodium hydroxide solution followed by neutralization with sulfuric acid or carbon dioxide, solvent extraction, pressurized crystallization, etc. The composition of the crude phenols obtained, however, is very complicated. For example, the phenols mixture extracted from the fraction with boiling range from 170 to 240° C. of one heavy coal tar contains 60 types of phenols, most of which have concentrations lower than 1 wt % of the whole coal tar, as reported by Wang et al. in "Extraction and GC/MS analysis of phenolic compounds in low temperature coal tar from Northern Shaanxi", J. of China Coal Society, 36 (4) (2011), 664-669. Some of these phenols also have very similar boiling points. This makes their separation and purification extremely difficult. In addition, only certain phenols, such as phenol, cresols, xylenols, naphthols and possibly methylnaphthols, have high volumes, have been widely used, and are therefore of economic interest.

Therefore, there is a need for a method of processing coal tar and other phenols containing feeds to obtain phenol and xylenes in a cost effective manner.

BRIEF DESCRIPTION OF THE DRAWINGS

The FIGURE illustrates one embodiment of a process according to the present invention.

DESCRIPTION OF THE INVENTION

It would be desirable to be able to process materials containing significant amounts of phenols to recover the phenols and/or to produce xylenes. By phenol containing feed streams we mean any hydrocarbonaceous or aqueous streams from pharmaceutical, chemical, or petroleum processes, which contain phenols in the range of 0.1 to 100 wt %, or 0.1 to 80%, or 0.1 to 60%, or 0.1 to 40%, or 1 to 40%, or 5 to 40%, or 5 to 30%. Suitable phenol containing feed streams include, but are not limited to, product streams like coal tar, light oil, bio-oil from the gasification and liquefaction of coal, wood, plant oil, and other biomass materials.

The alkylphenols in the crude phenols mixture, like the ones mentioned above, can be converted to phenol and/or naphthols for easy separation and use. Valuable products such as xylenes are also produced.

Although direct dealkylation may be employed to convert the alkylphenols, there can be a number of problems associated with the process. When direct dealkylation is done without a catalyst, the process temperature is in the range of 700 to 900° C. This can lead to the dealkylation of the phenols through thermal cracking at the high process temperature. It is quite energy intensive because of the high process temperature. In addition, it is normally not selective due to the loss of the hydroxyl group. Catalytic dealkylation can be done at much milder conditions. At temperatures from 300 to 400° C., ethylphenol and propylphenol can be dealkylated to produce phenol and ethylene/propylene on a ZSM-5 zeolite. However, water usually has to be co-fed to prevent severe catalyst deactivation. In addition, cresols dealkylation is relatively difficult, and phenol selectivity can be a concern.

In one embodiment, the present process involves reacting the crude alkylphenols with benzene or toluene in a transalkylation reaction in order to transfer the alkyl groups, such as methyl, ethyl, propyl, butyl, to benzene or toluene to form phenol and alkylbenzenes, such as toluene, xylenes, and heavy alkylbenzenes, such as ethylbenzene, propylbenzene, and butylbenzene. By "heavy alkylbenzenes," we mean ethylbenzene and other alkylbenzenes having molecular weight higher than that of xylenes. If the alkylphenols have double rings, naphthols will be the products after the transalkylation. The transalkylation of alkylphenols with aromatics such as toluene can be performed at very mild conditions (50-700° C., or 200-540° C.).

The benzene, toluene, and xylenes in the product stream of the transalkylation reaction are separated. In some embodiments, the benzene and toluene are taken off together and recycled to the transalkylation reaction zone. Alternatively, the benzene and toluene are taken off separately, with the benzene recycled to the transalkylation reaction zone, and the toluene sent to a disproportionation reaction zone to make xylenes.

The xylenes can be further processed through separation and isomerization to make p-xylene.

The remaining aromatic products in the transalkylation stream (heavy alkylbenzenes) are sent to a dealkylation reaction zone. Alkylbenzenes having alkyl groups containing two or more carbon atoms, such as ethyl, propyl, are dealkylated to form benzene and olefins, or paraffins if hydrogenation occurs during the dealkylation.

Overall, the main products will be phenol and/or naphthols, and xylenes, particularly, para-xylene, with light olefins or paraffins as the by-products.

The phenols-containing feed stream can be separated prior to the transalkylation reaction zone to facilitate the process. For example, coal tar can be fractionated and a portion in a certain boiling range used for phenol extraction. The crude phenols from whole coal tar may be pre-separated into single ring phenols and multi-ring phenols (2 and more rings) and reacted with benzene or toluene separately for easy processing (reaction and separation).

One aspect of the invention is a process for producing one or more of phenol, and xylenes. In one embodiments, the process comprises: introducing a phenols containing feed stream into a feed separation zone; separating the phenols containing feed stream in the feed separation zone into at least a phenol stream comprising phenol, and an alkylphenol stream comprising alkylphenols; transalkylating the alkylphenol stream and a reactant stream comprising one or more of benzene or toluene in a transalkylation reaction zone under transalkylation reaction conditions to produce a transalkylation effluent stream comprising phenols, and alkylbenzenes; separating the transalkylation effluent stream in a phenol separation zone into a phenol recycle stream comprising phenols, and an aromatic stream comprising benzene, toluene, xylenes, and heavy alkylbenzenes; separating the aromatic stream in an aromatic separation zone into at least a recycle stream comprising one or more of benzene or toluene, a heavy alkylbenzene stream comprising heavy alkylbenzenes, and a mixed xylene stream comprising mixed xylenes; separating the mixed xylene stream in a xylene separation zone into a second xylene stream comprising o-xylene and m-xylene, and a p-xylene stream comprising p-xylene; isomerizing the second xylene stream in an isomerization reaction zone under isomerization reaction conditions to form an isomerization effluent stream comprising mixed xylenes; and recovering one or more of the phenol stream and the p-xylene stream.

In some embodiments, separating the aromatic stream in the aromatic separation zone into at least the recycle stream comprising one or more of benzene or toluene, the heavy alkylbenzene stream comprising heavy alkylbenzenes, and the mixed xylene stream comprising mixed xylenes comprises separating the aromatic stream in the aromatic separation zone into at least the recycle stream comprising one or more of benzene or toluene, the heavy alkylbenzene stream comprising heavy alkylbenzenes, the mixed xylene stream comprising mixed xylenes, and a toluene stream comprising toluene, and further comprising one or more of: disproportionating the toluene stream in a disproportionation reaction zone under disproportionation reaction conditions to form a disproportionation effluent stream comprising xylenes, and recycling the disproportionation effluent stream to the aromatic separation zone; or recycling the toluene stream to the transalkylation reaction zone.

In some embodiments, the process further comprises: dealkylating the heavy alkylbenzene stream in a dealkylation reaction zone under dealkylation reaction conditions to form a dealkylation effluent stream comprising benzene, toluene, xylenes, heavy aromatics, hydrogen, and light hydrocarbons.

In some embodiments, the process further comprises: separating the dealkylation effluent stream in a dealkylation separation zone into a light gas stream comprising hydrogen and light hydrocarbons, and a second aromatic stream comprising benzene, toluene, xylenes, and heavy alkylbenzenes; and recycling the second aromatic stream to the aromatic separation zone.

In some embodiments, the process further comprises: separating the light gas stream in a gas separation zone into hydrogen stream comprising hydrogen and a light hydrocarbon gas stream comprising $C_2$-$C_4$ hydrocarbons; and recycling the hydrogen stream to the dealkylation reaction zone.

In some embodiments, the process further comprises: introducing a fresh hydrogen stream into the dealkylation reaction zone.

In some embodiments, the process further comprises one or more of: recycling the recycle stream to the transalkylation reaction zone; or recycling the isomerization effluent stream to the aromatic separation zone.

In some embodiments, the reactant stream comprises one or more of fresh benzene, recycled benzene, fresh toluene, or recycled toluene.

In some embodiments, separating the phenols containing feed stream comprises extracting a first fraction of the phenols containing feed stream into an extracted phenol stream comprising phenol and alkylphenols and a hydrocarbon stream.

In some embodiments, the process further comprises: fractionating the phenols containing feed stream into the first fraction and a second fraction comprising naphthols; and recovering the naphthols from the second fraction.

In some embodiments, the process further comprises: fractionating the extracted phenol stream into at least the alkylphenol stream and the phenol stream.

In some embodiments, the process further comprises purifying the phenol stream.

In some embodiments, the phenols containing feed stream comprises coal tar.

Another aspect of the invention is a process for producing one or more of phenol, and xylenes. In one embodiment, the process comprises: introducing a phenols containing feed stream into a feed separation zone; separating the phenols containing feed stream in the feed separation zone into at least a phenol stream comprising phenol and an alkylphenol stream comprising alkylphenols; transalkylating the alkylphenol stream and a reactant stream comprising one or more of benzene or toluene in a transalkylation reaction zone under transalkylation reaction conditions to produce a transalkylation effluent stream comprising phenols, and alkylbenzenes; separating the transalkylation effluent stream in a phenol separation zone into a phenol recycle stream comprising phenol, and an aromatic stream comprising benzene, toluene, xylenes, and heavy alkylbenzenes; separating the aromatic stream in an aromatic separation zone into at least a recycle stream comprising benzene, a toluene stream comprising toluene, a mixed xylene stream comprising mixed xylenes, and a heavy alkylbenzene stream comprising heavy alkylbenzenes; disproportionating the toluene stream in a disproportionation reaction zone under disproportionation reaction conditions to form a disproportionation effluent stream comprising xylenes; separating the mixed xylene stream in a xylene separation zone into a second xylene stream comprising o-xylene and m-xylene, and a p-xylene stream comprising p-xylene; isomerizing the second xylene stream in an isomerization reaction zone under isomerization reaction conditions to form an isomerization effluent stream comprising mixed xylenes; dealkylating the heavy alkylbenzene stream in a dealkylation reaction zone under dealkylation reaction conditions to form a dealkylation effluent stream comprising benzene, toluene, xylenes, heavy aromatics, hydrogen and light hydrocarbons; and recovering one or more of the phenol stream and the p-xylene stream.

In some embodiments, the process further comprises one or more of: recycling the benzene stream to the transalkylation reaction zone; recycling the disproportionation effluent stream to the aromatic separation zone; or recycling the isomerized xylene stream to the aromatic separation zone.

In some embodiments, the process further comprises: separating the dealkylation effluent stream in a dealkylation separation zone into a light gas stream comprising hydrogen and light hydrocarbons, and a second aromatic stream comprising benzene, toluene, xylenes, and heavy aromatics; and recycling the second aromatic stream to the aromatic separation zone.

In some embodiments, the process further comprises: separating the light gas stream in a gas separation zone into hydrogen stream comprising hydrogen and a light hydrocarbon gas stream comprising $C_2$-$C_4$ hydrocarbon stream; and recycling the hydrogen stream to the dealkylation reaction zone.

In some embodiments, separating the phenols containing feed stream comprises extracting a first fraction of the phenols containing feed stream into an extracted phenol stream comprising phenol and alkylphenols and a hydrocarbon stream.

In some embodiments, the process further comprises: fractionating the phenols containing feed stream into the first fraction and a second fraction comprising naphthols; and recovering the naphthols from the second fraction.

In some embodiments, the process further comprises: fractionating the extracted phenol stream into at least the alkylphenol stream and the phenol stream.

The FIGURE illustrates one embodiment of a process 100. For convenience, the process 100 will be discussed using a coal tar feed stream 105. Those of skill in the art will recognize that other phenol-containing feeds could be used. The coal tar feed stream 105 containing phenols is sent to the feed separation zone 110. In the embodiment shown in the FIGURE, the feed separation zone 110 includes a first fractionation zone 115, an extraction zone 120, and a second fractionation zone 125. The coal tar feed stream 105 is fractionated in the first fractionation zone 115. The first fraction 130 with a boiling point below 245° C. is fed to the extraction zone 120, while the second fraction 135 with a boiling point above 245° C. may be sent for further processing.

The first fraction 130 is separated in the extraction zone 120 into a hydrocarbon stream 140 and an extracted phenol stream 145. The extracted phenol stream 145 comprises phenol and alkylphenols. The extracted phenol stream 145 is sent to the second fractionation zone 125 where it is separated into at least an alkylphenols stream 150 comprising alkylphenols, and a phenol stream 155 comprising phenol.

The alkylphenols stream 150 is fed to a transalkylation reaction zone 160 along with a reactant stream 170. Reactant stream 170 can comprise benzene and/or toluene. Reactant stream 170 can comprise fresh stream 175 comprising fresh benzene and/or toluene, and/or recycle stream 180 which comprises recycled benzene. The alkylphenols and benzene are transalkylated to produce a transalkylation effluent stream 185 comprising phenol and alkylbenzenes.

When a catalyst is used for transalkylation, the temperature is typically in the range of 50 to 700° C., or 200 to 540° C. The transalkylation zone is typically operated at pressures ranging from about 100 kPa(a) to 6 MPa(a) or 150 kPa(a) to 3 MPa(a). The weight hourly space velocity (WHSV) is generally in the range of 0.1 to 20 hr$^{-1}$, or 0.2 to 10 hr$^{-1}$ The catalyst is typically selected to have relatively high stability at a high activity level. Suitable transalkylation catalysts include, but are not limited to zeolites, acidic clay, silica alumina, acidic resins, mixed metal oxides, and the like as are known in the art.

Ratios of benzene/toluene to phenol (molar ratio) is 0.1:1 to 20:1, or 0.5:1 to 10:1, or 1:1 to 5:1.

The transalkylation effluent stream 185 is sent to a phenols separation zone 190 where it is separated into a phenols recycle stream 195 comprising phenols and an aromatics stream 200 comprising benzene, toluene, xylenes, and heavy alkylbenzenes. The phenols recycle stream 195 is recycled to the feed separation zone 110 where it can be sent to the second fractionation zone 125. The phenols recycle stream 195 can be sent directly to the second fractionation zone 125, or it can be combined with the extracted phenol stream 145, and the combined stream can be sent to the second fractionation zone 125.

The aromatics stream 200 is sent to the aromatics separation zone 205 where it is separated into a recycle benzene stream 180 comprising benzene, optionally a toluene stream 210 comprising toluene, a mixed xylenes stream 215 comprising p-xylene, o-xylene, and m-xylene, and a heavy alkylbenzene stream 220 comprising heavy alkylbenzenes.

The recycle stream 180 can be sent back to the transalkylation reaction zone 160.

The toluene stream 210 is sent to a disproportionation reaction zone 225 with hydrogen stream 227 where the toluene is disproportionated to form a disproportionation effluent 230 comprising xylenes and benzene. Conditions employed in the disproportionation process zone normally include a temperature of 200° to 600° C., or 350° to 575° C. The temperature required to maintain the desired degree of conversion will increase as the catalyst gradually loses activity during processing. Normal end-of-run temperatures may therefore exceed start-of-run temperatures by 65° C. or more. The disproportionation zone is generally operated at hydrogen-to-hydrocarbon ratios of 0.1:1 to about 3.0:1, or 1:1, or 0.2:1 to 0.5:1. The ratio of hydrogen-to-hydrocarbon is calculated based on the molar ratio of free hydrogen compared against the feedstock hydrocarbon. Periodic increases in hydrogen-to-hydrocarbon above 0.5:1, and preferably in the range of 1:1 to 5:1 permit catalyst rejuvenation by hydrogenation of soft coke. The disproportionation zone is operated at moderately elevated pressures broadly ranging from about 100 kPa(a) to 6 MPa(a) or 2 to 3.5 MPa(a). The disproportionation reaction can be effected over a wide range of space velocities, with higher space velocities effecting a higher ratio of para-xylene at the expense of conversion. The LHSV generally is in the range of from about 0.2 to 20 hr$^{-1}$.

The disproportionation effluent 230 is sent back to the aromatic separation zone 205. Hydrogen can be separated from the disproportionation effluent 230 and recycled (not shown), as in known in the art.

In some embodiments, the toluene is fractionated with the benzene. In this case, the recycle stream 180 comprises benzene and toluene, and it is recycled back to the transalkylation zone 160.

The mixed xylenes stream 215 is sent to a xylene separation zone 235 where it is separated into a p-xylene stream 240 comprising p-xylene and a second mixed xylene stream 245 comprising o-xylene and m-xylene.

The second mixed xylene stream 245 and hydrogen stream 252 are sent to the isomerization reaction zone 250 where the o-xylene and m-xylene are isomerized to form an isomerization zone effluent 255. Isomerization conditions comprise a temperature of from about 100° to 600° C. or 150° to 500° C., a pressure of from about 10 kPa(a) to 5 MPa(a), a WHSV of from about 0.5 to 100 hr$^{-1}$, or 1 to 50 hr$^{-1}$.

The isomerization zone effluent 255 is sent to aromatic separation zone 205. Hydrogen can be separated from the isomerization effluent 255 and recycled (not shown), as in known in the art.

The heavy alkylbenzene stream 220 and hydrogen stream 262 are sent to a dealkylation reaction zone 260 where the heavy alkylbenzenes are dealkylated to form a dealkylation reaction zone effluent 265 comprising benzene, unreacted heavy alkylbenzenes, hydrogen, and paraffins.

The dealkylation reaction zone effluent 265 is sent to a dealkylation separation zone 270 where it is separated into a light gas stream 275 comprising hydrogen and light hydrocarbons and a second aromatics stream 280 comprising benzene and unreacted heavy alkylbenzenes.

In some embodiments, the dealkylation reaction conditions comprise at least one of: a temperature in a range of 100-700° C. in the presence of a catalyst; a temperature in a range of 400-900° C. in the absence of a catalyst; a pressure in a range of 1-5 MPa(a); or a LHSV of 1-5 h$^{-1}$. Dealkylation reactions can also performed under vacuum, for example, typically 50 kPa(a), with a maximum of 20 kPa(a), if desired.

Hydrogen can be co-fed to the dealkylation reaction zone to minimize catalyst deactivation. Hydrogen to hydrocarbon ratios typically range from 0.1:1 to 10:1, or 1:1 to 4:1.

The second aromatics stream 280 is recycled to the aromatic separation zone 205.

The light gas stream 275 is sent to gas separation zone 285 where it is separated into a hydrogen stream 290 comprising hydrogen, and a light hydrocarbon stream comprising $C_2$-$C_4$ hydrocarbons. Hydrogen stream 290 can be recycled to the dealkylation reaction zone 260. Optionally, fresh hydrogen stream 300 can be added to the hydrogen stream 290.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for producing one or more of phenol, and xylenes comprising:
    introducing a phenols containing feed stream into a feed separation zone;
    separating the phenols containing feed stream in the feed separation zone to obtain a phenol stream comprising phenol, and a crude alkylphenol stream comprising alkylphenols;
    transalkylating the crude alkylphenol stream and a reactant stream comprising one or more of benzene or toluene in a transalkylation reaction zone under transalkylation reaction conditions to produce a transalkylation effluent stream comprising phenols, and alkylbenzenes;
    separating the transalkylation effluent stream in a phenol separation zone into a phenol recycle stream comprising phenols, and an aromatic stream comprising benzene, toluene, xylenes, and heavy alkylbenzenes;
    separating the aromatic stream in an aromatic separation zone into at least a recycle stream comprising one or more of benzene or toluene, a heavy alkylbenzene stream comprising heavy alkylbenzenes, and a mixed xylene stream comprising mixed xylenes;
    separating the mixed xylene stream in a xylene separation zone into a second xylene stream comprising o-xylene and m-xylene, and a p-xylene stream comprising p-xylene;
    isomerizing the second xylene stream in an isomerization reaction zone under isomerization reaction conditions to form an isomerization effluent stream comprising mixed xylenes; and
    recovering one or more of the phenol stream and the p-xylene stream.

2. The process of claim 1 wherein separating the aromatic stream in the aromatic separation zone into at least the recycle stream comprising one or more of benzene or toluene, the heavy alkylbenzene stream comprising heavy alkylbenzenes, and the mixed xylene stream comprising mixed xylenes comprises separating the aromatic stream in the aromatic separation zone into at least the benzene stream comprising benzene, the heavy alkylbenzene stream comprising heavy alkylbenzenes, the mixed xylene stream comprising mixed xylenes, and a toluene stream comprising toluene, and further comprising one or more of:
    disproportionating the toluene stream in a disproportionation reaction zone under disproportionation reaction conditions to form a disproportionation effluent stream comprising xylenes, and recycling the disproportionation effluent stream to the aromatic separation zone; or
    recycling the toluene stream to the transalkylation reaction zone.

3. The process of claim 1 further comprising:
    dealkylating the heavy alkylbenzene stream in a dealkylation reaction zone under dealkylation reaction conditions to form a dealkylation effluent stream comprising benzene, toluene, xylenes, heavy aromatics, hydrogen and light hydrocarbons.

4. The process of claim 3 further comprising:
    separating the dealkylation effluent stream in a dealkylation separation zone into a light gas stream comprising hydrogen and light hydrocarbons, and a second aromatic stream comprising benzene, toluene, xylenes, and heavy alkylbenzenes; and
    recycling the second aromatic stream to the aromatic separation zone.

5. The process of claim 4 further comprising:
    separating the light gas stream in a gas separation zone into hydrogen stream comprising hydrogen and a light hydrocarbon gas stream comprising C2-C4 hydrocarbons; and
    recycling the hydrogen stream to the dealkylation reaction zone.

6. The process of claim 3 further comprising:
    introducing a fresh hydrogen stream into the dealkylation reaction zone.

7. The process of claim 1 further comprising one or more of:
    recycling the recycle stream to the transalkylation reaction zone; or
    recycling the isomerization effluent stream to the aromatic separation zone.

8. The process of claim 1 wherein the reactant stream comprises one or more of fresh benzene, recycled benzene, fresh toluene, or recycled toluene.

9. The process of claim 1 wherein separating the phenols containing feed stream comprises extracting a first fraction of the phenols containing feed stream into an extracted phenol stream comprising phenol and alkylphenols and a hydrocarbon stream.

10. The process of claim 9 further comprising:
    fractionating the phenols containing feed stream into the first fraction and a second fraction comprising naphthols; and
    recovering the naphthols from the second fraction.

11. The process of claim 1 further comprising:
fractionating the extracted phenol stream into at least the alkylphenol stream and the phenol stream.

12. The process of claim 1 further comprising purifying the phenol stream.

13. The process of claim 1 wherein the phenols containing feed stream comprises coal tar.

14. A process for producing one or more of phenol, and xylenes comprising:
introducing a phenols containing feed stream into a feed separation zone;
separating the phenols containing feed stream in the feed separation zone to obtain a phenol stream comprising phenol and a crude alkylphenol stream comprising alkylphenols;
transalkylating the crude alkylphenol stream and a reactant stream comprising one or more of benzene or toluene in a transalkylation reaction zone under transalkylation reaction conditions to produce a transalkylation effluent stream comprising phenols, and alkylbenzenes;
separating the transalkylation effluent stream in a phenol separation zone into a phenol recycle stream comprising phenol, and an aromatic stream comprising benzene, toluene, xylenes, and heavy alkylbenzenes;
separating the aromatic stream in an aromatic separation zone into at least a recycle stream comprising benzene, a toluene stream comprising toluene, a mixed xylene stream comprising mixed xylenes, and a heavy alkylbenzene stream comprising heavy alkylbenzenes;
disproportionating the toluene stream in a disproportionation reaction zone under disproportionation reaction conditions to form a disproportionation effluent stream comprising xylenes;
separating the mixed xylene stream in a xylene separation zone into a second xylene stream comprising o-xylene and m-xylene, and a p-xylene stream comprising p-xylene;
isomerizing the second xylene stream in an isomerization reaction zone under isomerization reaction conditions to form an isomerization effluent stream comprising mixed xylenes;
dealkylating the heavy alkylbenzene stream in a dealkylation reaction zone under dealkylation reaction conditions to form a dealkylation effluent stream comprising benzene, toluene, xylenes, heavy aromatics, hydrogen and light hydrocarbons; and
recovering one or more of the phenol stream and the p-xylene stream.

15. The process of claim 14 further comprising one or more of:
recycling the recycle stream to the transalkylation reaction zone;
recycling the disproportionation effluent stream to the aromatic separation zone; or
recycling the isomerized xylene stream to the aromatic separation zone.

16. The process of claim 14 further comprising:
separating the dealkylation effluent stream in a dealkylation separation zone into a light gas stream comprising hydrogen and light hydrocarbons, and a second aromatic stream comprising benzene, toluene, xylenes, and heavy aromatics; and
recycling the second aromatic stream to the aromatic separation zone.

17. The process of claim 16 further comprising:
separating the light gas stream in a gas separation zone into hydrogen stream comprising hydrogen and a light hydrocarbon gas stream comprising C2-C4 hydrocarbon stream; and
recycling the hydrogen stream to the dealkylation reaction zone.

18. The process of claim 14 wherein separating the phenols containing feed stream comprises extracting a first fraction of the phenols containing feed stream into an extracted phenol stream comprising phenol and alkylphenols and a hydrocarbon stream.

19. The process of claim 18 further comprising:
fractionating the phenols containing feed stream into the first fraction and a second fraction comprising naphthols; and
recovering the naphthols from the second fraction.

20. The process of claim 18 further comprising:
fractionating the extracted phenol stream into at least the alkylphenol stream and the phenol stream.

* * * * *